United States Patent [19]

Oka et al.

[11] Patent Number: 6,054,125
[45] Date of Patent: Apr. 25, 2000

[54] PURIFIED MITE ALLERGEN

[75] Inventors: Satoru Oka; Kazuhisa Ono, both of Hiroshima; Seiko Shigeta; Takeshi Wada, both of Hiroshima-ken, all of Japan

[73] Assignees: Fumakilla Limited, Tokyo; Hiroshima University, Hiroshima-ken, both of Japan

[21] Appl. No.: 09/009,835

[22] Filed: Jan. 20, 1998

Related U.S. Application Data

[62] Division of application No. 08/293,605, Aug. 22, 1994, Pat. No. 5,747,047, which is a continuation of application No. 07/846,935, Mar. 6, 1992, abandoned.

[30] Foreign Application Priority Data

Mar. 9, 1991 [JP] Japan ..................................... 3-104950

[51] Int. Cl.$^7$ .......................... A61K 39/00; A61K 39/38; A61K 39/35; A61K 39/36; C07K 14/00
[52] U.S. Cl. ..................................... 424/184.1; 424/275.1; 424/276.1; 530/350; 530/395; 530/412
[58] Field of Search .............................. 424/184.1, 275.1, 424/276.1; 530/350, 395, 412

[56] References Cited

U.S. PATENT DOCUMENTS

| | | |
|---|---|---|
| 5,314,991 | 5/1994 | Oka et al. . |
| 5,405,758 | 4/1995 | Oka et al. . |
| 5,496,554 | 3/1996 | Oka et al. . |
| 5,747,047 | 5/1998 | Oka et al. . |
| 5,773,010 | 6/1998 | Oka et al. . |

FOREIGN PATENT DOCUMENTS

047311A2  9/1991  European Pat. Off. .

OTHER PUBLICATIONS

Daneu, J.P. et al., Immunology 46:679–687 (1982).
Lind et al. Scand J. Immunol. 17:263–273 (1983).
Le Mao, J. et al., Immunol 44:239–247 (1981).
Chua et al, *Int. Arch. Appl. Immunol.* 91:118–123 (1990).
Chua et al, *Int. Arch. Appl. Immunol.* 91:124–129 (1990).
Yuuki et al, *Agric. Biol. Chem.* 55(5):1233–1238 (1991).
Thomas et al, *Int Archs. Allergy Appl. Immun.* 85:127–129 (1988).
Chua et al. *J. Exp. Med.* 167:175–182 (1988).
Tovey et al. *J. Exp.Med.* 170:1457–1462 (1989).
Yuuki et al, *Jpn. J. Allergol.* 39(6):557–561 (1990).
Andersen, Int. Arch. Allerg. Appl. Immunol. 89:17–23 (1989).
Lin et al. Annals of Allergy 67:63–69 (Jul. 1991).
Roitt et al, "Hypersensitivity Type I" pp. 19.16–19.17 in *Immunology*, c. 1985 by Gower Med. Publishing Co. Ltd. St. Louis Mo.
Tovey et al, Comparison by electroblotting of IgE binding components, J. Allerg. Clin. Immunol 79:93–102 (1987).
Heyman et al, Antigen Derfl from the dust mite *Dermatophagoides farinae*: J. Immunol 137:2841–47.
Krilis et al, Antigens and Allergens from the common house, J. Allergy Clin. Immunol. 74:132–41.
Colloff et al., Int Arch. Allergy Immunol. 97: 44–49 (1992).
Gaddie et al, British Medical Journal pp. 561–562, 1976.
Aki et al Int. Arch. Allergy Immunol 103:357–364, 1994.
Chapman et al., *Clin. Exp. Immunol.*, 34:126–136 (1978).
Kabasawa et al., *Jpn. J. Exp. Med.*, 49(1):51–57 (1979).
Baldo et al., *Advances in Biosciences*, 74–13–31.
Tanaka et al., Annual Meeting of Japan Society of Agricultural Chemistry 62:411 Abstract No. 2Wp5 (1989).
Oka et al., Annual Meeting of Japan Society of Agricultural Chemistry 63:280–281 Abstract No. 3Ga22 (1989) .
Garfin, *Methods in Enzymology*, 182:425–428 (1990).
Stewart, *Int. Arch. Allergy Appl. Immun.*, 69:224–230 (1982).
Trudinger et al., *Clin. Exp. Allergy*, 21:33–37 (1991).
Chemical Abstracts vol. 115, No. 7, pp. 631, Abstract No. 69823f (1991).
Yuuki et al., *Int. Archs. Allergy Appl. Immun.*, 94:354–356 (1991).

*Primary Examiner*—Nita Minnifield
*Attorney, Agent, or Firm*—Birch, Stewart, Kolasch & Birch, LLP

[57] ABSTRACT

The present invention is directed to novel purified and isolated mite allergens possessing mite allergen activity with a molecular weight of about 94,000, about 40,000, about 16,000 or about 14,000 as determined by SDS-PAGE, which can be isolated from extracts of mites, and to a process for producing such mites allergens. The purified and isolated mite allergens of the present invention are useful as a pharmaceutical and a diagnostic composition for mite allergic diseases.

7 Claims, 4 Drawing Sheets

PURIFIED MITE ALLERGEN

This application is divisional application Ser. No. 08/293,605, filed on Aug. 22, 1994 now U.S. Pat. No. 5,747,097, which is in turn a continuation of Ser. No. 07/846,935, filed Mar. 6, 1992 now abandoned. The entire contents of both of these applications are hereby incorporated by reference.

FIELD OF THE INVENTION

The present invention relates to a purified mite allergen possessing allergen activity and more specifically to a new glycoprotein possessing allergen activity contained in extracts of mite.

BACKGROUND OF THE INVENTION

House dust mites are important as a major causative factor of allergic diseases such as atopic bronchial asthma. Traditionally, hyposensitization therapy has been the most important radical therapy for allergic diseases, in which patients are hyposensitized by administration of allergen, the substance which causes allergy. Specifically, in diseases in which antigen identification is easy, such as pollinosis and insect allergy, hyposensitization therapy can be said to have already been highly valued. This therapy, however, necessitates administration of a safe therapeutic antigen because it involves a risk of anaphylaxis due to allergen.

Two mite species, namely *Dermatophagoides pteronyssinus* and *Dermatophagoides farinae*, are reported to play a major role as house dust mite allergens in mite allergic diseases [J. Allergy: 42, 14–28 (1968)]. The major mite allergen which have so far been reported include glycoproteins with a molecular weight of 24 to 28 kD (pI 4.6 to 7.2) and/or proteins with a molecular weight of 14.5 to 20 kD (pI 5 to 8.3), both contained in mite feces and/or mites [e.g. J. Immunol.: 125, 587–592(1980)/J. Allergy Clin. Immunol.: 76, 753–761(1985)/Immunology: 46, 679–687 (1982)/Int. Arch. Allergy Appl. Immunol.: 81, 214–223(1986)/J. Allergy Clin. Immunol.: 75, 686–692(1985)].

On the other hand, the present inventors reported the presence of components which exhibit specific reactivity to serum IgG of mite asthmatic patients and which induce leukocyte histamine release in mite asthmatic patients in fractions with higher molecular weight and those with lower molecular weight in comparison with the above-mentioned major mite allergens [The Annual Meeting of the Japan Society of Agricultural Chemistry: 62, 411 (1988)]. These components, however, remained to be purified to a degree such that they can be used as antigens for hyposensitization therapy.

Mite allergic diseases have been diagnosed mainly on the basis of inquiry in combination with skin reaction tests using a house dust extract and/or mite extract in most cases, with measurements of serum IgE antibody titer (relative values) taken by the RAST method used in only a very few cases; it has been very difficult to make direct diagnoses of mite allergic diseases.

Traditionally, house dust extract solutions have been used for hyposensitization therapy for bronchial asthma involving house dust mites as specific antigens; however, their dose is subject to extreme limitation and their therapeutic effect is extremely low, since they are very indefinite in chemical composition and contain a wide variety of impurities which may induce anaphylaxis. Therefore, from the viewpoint of efficacy and safety, it is desired that a valuable antigen for hyposensitization therapy will be developed.

Also, it is important to make quick and accurate diagnoses of mite allergic diseases in appropriate treatment of mite allergic diseases; a new diagnostic system is expected to be well established.

SUMMARY OF THE INVENTION

The object of the present invention is to provide a new purified and isolated mite allergen which is very valuable for use as a remedy and a diagnostic drug.

Accordingly, it is an object of the present invention to provide a novel purified and isolated mite allergen substantially free of any other mite proteins, possessing allergen activity which can be isolated from extracts of mites.

It is another object of the present invention to provide a process for producing said novel purified and isolated mite allergen.

It is still another object of the present invention to provide a novel remedy for mite allergic diseases.

It is yet another object of this invention to provide a novel diagnostic drug for mite allergic diseases.

With the aim of accomplishing these objects, the present inventors made intensive investigations of allergens contained in extracts of *Dermatophagoides farinae*, and found that glycoproteins with molecular weights of about 94,000, about 40,000, about 16,000 and about 14,000 possess potent allergen activity. The present inventors made further investgations based on this finding, then developing the present invention. Accordingly, the present invention comprises purified and isolated mite allergens substantially free of any other mite proteins possessing the following physicochemical and biological properties:

i) purified and isolated mite allergen
  ① being contained in extracts of mites,
  ② glycoprotein containing about 60% sugar,
  ③ a molecular weight of about 94,000 as determined by SDS-PAGE (SDS-polyacrylamide gel electrophoresis),
  ④ possessing allergen activity, ii) purified and isolated mite allergen
  ① being contained in extracts of mites,
  ② glycoprotein containing about 15% sugar,
  ③ a molecular weight of about 40,000 as determined by SDS-PAGE,
  ④ possessing allergen activity, iii) purified and isolated mite allergen
  ① being contained in extracts of mites,
  ② glycoprotein containing about 20% sugar,
  ③ a molecular weight of about 16,000 as determined by SDS-PAGE,
  ④ possessing allergen activity, iv) purified and isolated mite allergen
  ① being contained in extracts of mites,
  ② glycoprotein containing about 13% sugar,
  ③ a molecular weight of about 14,000 as determined by SDS-PAGE,
  ④ possessing allergen activity.

The present invention also comprises a process for producing the above-mentioned mite allergens which comprises, in the order mentioned, the steps of:

suspending mites in culture with a saturated sodium chloride solution and keeping the suspension standing;

collecting said mites from a the resulting from centrifugation of the suspension;

grinding the collected mites;

extracting a mite allergen with a buffer with a moderate ionic strength from the ground mites; and fractionating said extracts and isolating a glycoprotein fraction which possesses mite allergen activity.

The present invention further comprises a remedy for mite allergic diseases and a diagnostic drug for mite allergic diseases, both containing the above-mentioned mite allergen as active ingredient.

DETAILED DESCRIPTION OF THE INVENTION

Figure 1:
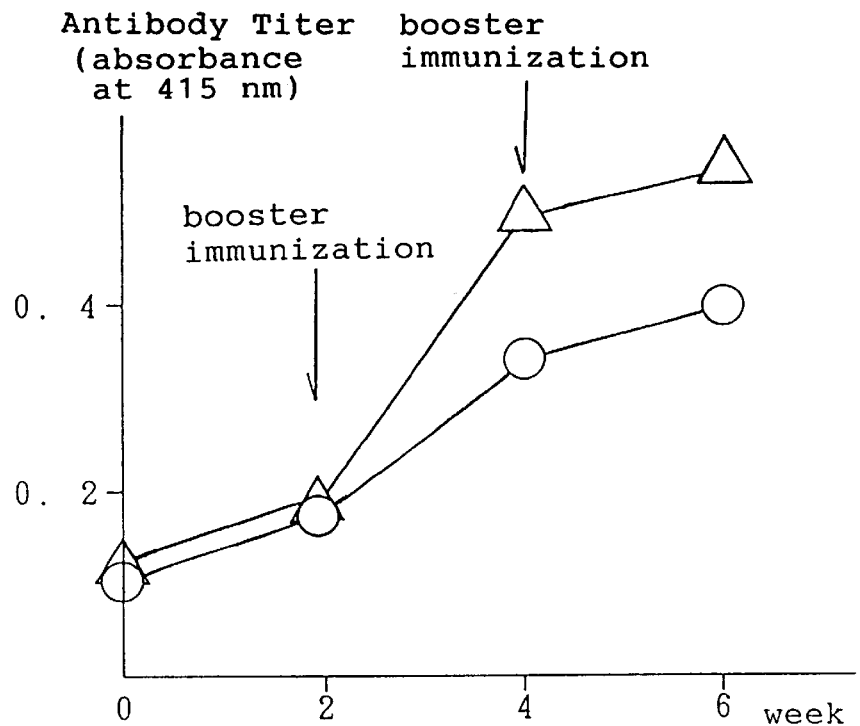
FIG. 1 shows changes in antibody titer (IgG) in mice immunized with Dfb-94.

In the present specification, amino acids, etc. are sometimes represented by abbreviations based on the IUPAC-IUB NomencLature and those which are commonly used in relevant fields. Their examples are given below.

Abbreviations for amino acid residues are as follows:

| | | | |
|---|---|---|---|
| Asx | aspartic acid and/or asparagine; | | |
| Thr | threonine; | Ser | serine |
| Glx | glutamic acid and/or glutamine | | |
| Gly | glycine; | Ala | alanine; |
| Val | valine; | Ile | isoleucine; |
| Leu | leucine; | Tyr | tyrosine; |
| Phe | phenylalanine; | His | histidine; |
| Lys | lysine; | Arg | arginine; |
| Pro | proline; | Cys | cysteine; |
| Met | methionine | | |

Abbreviations for sugars are as follows:

| | | | |
|---|---|---|---|
| Fuc | Fucose; | Ara | Arabinose; |
| Xyl | Xylose; | Gal | Galactose; |
| Man | Mannose; | Glc | Glucose; |
| HexNAc | N-acetylhexosamine | | |

It does not matter whether the purified and isolated mite allergen of the present invention comprises a single purified and isolated mite allergen or a number of purified and isolated mite allergens (i.e., in the form of a mixture of purified and isolated mite allergens), as long as it meets the above-mentioned requirements of ① through ④, respectively.

Some representative examples of the purified and isolated mite allergens of the present invention which are substantially free of any other mite proteins are hereinafter described in more detail.

i) Purified and isolated mite allergen (Dfb-94)

(1) Color and appearance: White (lyophilized product)

(2) Water solubility: Freely soluble (3) Molecular weight: About 94,000 as determined by SDS-PAGE (4) Composition: A sugar content of about 60% as determined by compositional analysis

[Amino acid composition]

200 μl of a 0.2% sample solution was mixed with 200 μl of 12N HCl and hydrolyzed at 110° C. in a sealed $N_2$-saturated test tube for 24 hours. After evaporating the hydrolysate to dryness, a small amount of water was added, and this was followed by re-evaporation to dryness. This procedure was repeated in three cycles to remove the hydrochloric acid. The resulting dry product was dissolved in 1 ml of a dilution buffer for amino acid analysis. This solution was then assayed using an amino acid analyzer (produced by Beckman Co.).

[Sugar composition]

Total neutral sugar was quantitatively determined by the phenol sulfuric acid method using glucose as reference substance.

Each neutral sugar and amino sugar was quantitatively determined by the GLC method after the sample was hydrolyzed at 100° C. in 4N TFA (trifluoroacetic acid) for 4 hours, reduced with $NaBH_4$, and then acetylated by heating at 100° C. for 4 hours in the presence of acetic anhydride.

| Amino acid (total 3260.1 nmol/mg) | | | | | |
|---|---|---|---|---|---|
| Asp | 413.2; | Thr | 461.0; | Ser | 298.0; |
| Glu | 521.4; | Gly | 127.8; | Ala | 150.4; |
| Cys | 21.5; | Val | 212.5; | Met | 19.4; |
| Ile | 77.0; | Leu | 370.4; | Tyr | 3.3; |
| Phe | 55.7; | His | 30.3; | Lys | 322.2; |
| Arg | 68.3; | Pro | 107.7 | | |

| Neutral sugar (total 3154.9 nmol/mg) | | | | | |
|---|---|---|---|---|---|
| Fuc | 216.5; | Ara | 426.7; | Xyl | 490.0; |
| Gal | 350.0; | Man | 1671.7; | Glc | — |

| Amino sugar (total 265.2 nmol/mg) | |
|---|---|
| HexNAc | 265.2 |

(5) Possesses allergen activity.

To be judged on the basis of skin reactivity to mite allergy patients and results of a patient leukocyte histamine release test using HPLC.

(6) Does not induce anaphylactic reaction.

Guinea pigs immunized by a standard method are observed for anaphylactic reaction at the time of booster immunization.

ii) Purified and isolated mite allergen (Dfb-40)

(1) Color and appearance: White (lyophilized product)

(2) Water solubility: Freely soluble (3) Molecular weight: About 40,000 as determined by SDS-PAGE (4) Composition: A sugar content of about 15% as determined by compositional analysis described above.

| Amino acid (total 6792.9 nmol/mg) | | | | | |
|---|---|---|---|---|---|
| Asp | 613.1; | Thr | 361.0; | Ser | 483.3; |
| Glu | 846.4; | Gly | 676.4; | Ala | 875.4; |
| Cys | 81.7; | Val | 511.1; | Met | 10.7; |

-continued

| Ile | 273.6; | Leu | 540.4; | Tyr | 93.3; |
| Phe | 212.5; | His | 147.6; | Lys | 433.7; |
| Arg | 334.7; | Pro | 298.0 | | |

| Neutral sugar (total 797.4 nmol/mg) | | | | | |
|---|---|---|---|---|---|
| Fuc | 12.2; | Ara | 28.7; | Xyl | 153.3; |
| Gal | 79.4; | Man | 469.4; | Glc | 54.4 |

| Amino sugar (total 67.4 nmol/mg) | |
|---|---|
| HexNAc | 67.4 |

(5) Possesses allergen activity.

To be judged on the basis of skin reactivity to mite allergy patients and results of a patient leukocyte histamine release test using HPLC.

(6) Does not induce anaphylactic reaction.

Guinea pigs immunized by a standard method are observed for anaphylactic reaction at the time of booster immunization.

iii) Purified and isolated mite allergen (Dfb-16)

(1) Color and appearance: White (lyophilized product)

(2) Water solubility: Freely soluble (3) Molecular weight: About 16,000 as determined by SDS-PAGE (4) Composition: A sugar content of about 20% as determined by compositional analysis described above.

| Amino acid (total 6378.4 nmol/mg) | | | | | |
|---|---|---|---|---|---|
| Asp | 753.6; | Thr | 569.3; | Sep | 530.0; |
| Glu | 728.1; | Gly | 523.3; | Ala | 456.8; |
| Cys | 64.4; | Val | 428.3; | Met | 12.7; |
| Ile | 310.2; | Leu | 424.5; | Tyr | 164.5; |
| Phe | 191.7; | His | 122.4; | Lys | 407.0; |
| Arg | 350.2; | Pro | 341.4 | | |

| Neutral sugar (total 778.4 nmol/mg) | | | | | |
|---|---|---|---|---|---|
| Fuc | 47.6; | Ara | 48.0; | Xyl | 320.7; |
| Gal | 182.7; | Man | —  | Glc | 179.4 |

| Amino sugar (total 290.5 nmol/mg) | |
|---|---|
| HexNAc | 290.5 |

(5) Possesses allergen activity.

To be judged on the basis of skin reactivity to mite allergy patients and results of a patient leukocyte histamine release test using HPLC.

(6) Does not induce anaphylactic reaction.

Guinea pigs immunized by a standard method are observed for anaphylactic reaction at the time of booster immunization.

iv) Purified and isolated mite allergen (Dfb-14)

(1) Color and appearance: White (lyophilized product)

(2) Water solubility: Freely soluble (3) Molecular weight: About 14,000 as determined by SDS-PAGE (4) Composition: A sugar content of about 13% as determined by compositional analysis described above.

| Amino acid (total 6601.5 nmol/mg) | | | | | |
|---|---|---|---|---|---|
| Asp | 722.8; | Thr | 715.4; | Ser | 577.5; |
| Glu | 870.2; | Gly | 471.4; | Ala | 576.9; |
| Cys | 59.4; | Val | 355.8; | Met | 76.4; |
| Ile | 281.3; | Leu | 554.1; | Tyr | 15.5; |
| Phe | 72.8; | His | 130.2; | Lys | 500.7; |
| Arg | 237.1; | Pro | 384.0 | | |

| Neutral sugar (total 564.3 nmol/mg) | | | | | |
|---|---|---|---|---|---|
| Fuc | 37.8; | Ara | 20.0; | Xyl | 219.3; |
| Gal | 66.1; | Man | 32.8; | Glc | 188.3 |

| Amino sugar (total 184.2 nmol/mg) | |
|---|---|
| HexNAc | 184.2 |

(5) Possesses allergen activity.

To be judged on the basis of skin reactivity to mite allergy patients and results of a patient leukocyte histamine release test using HPLC.

(6) Does not induce anaphylactic reaction.

Guinea pigs immunized by a standard method are observed for anaphylactic reaction at the time of booster immunization.

[Method for production]

Examples of the process for producing the purified and isolated mite allergens of the present invention include the following:

a) Preparation of Crude Mite Antigen

Any of *Dermatophagoides farinae* or *Dermatophagoides pteronyssinus* may be used as the starting material for the production of mite antigen. These mite species are cultured in a mite culture medium, and a crude antigen is extracted from the mites.

The treatment of the extract is carried out as follows. After adding a saturated sodium chloride solution, the culture is stirred, kept standing at room temperature for 30 minutes and than centrifuged (3000 rpm, 30 minutes), and the supernatants are pooled. The mites suspended in the pooled supernatant are collected by filtration. This procedure is repeated twice. These collected mites are ground together with the solvent, followed by centrifugation, and the resulting supernatant is dialyzed and lyophilized to yield a crude mite antigen (starting material). In this case, any other extracting solvent can be used, as long as it is a buffer having a moderate ionic strength. Examples of such buffer include lactate buffers, acetate buffers, citrate buffers, Tris-HCl buffer and borate buffers.

b) Purification of Crude Mite Antigen

The crude mite antigen can be purified and isolated by known ordinary methods of protein purification such as gel filtration chromatography, ultrafiltration, ion exchange chromatography, affinity chromatography, hydrophobic chromatography, isoelectric focusing and gel electrophoresis. These methods can be used singly or in combination. In this purification the elution pattern is monitored by:

(i) assay of the antigeneic activity of each fraction by enzyme-linked immunosorbent assay (ELISA) of reactivities to mite asthmatic patient serum specific IgE and IgG, rabbit anti-mite serum, rabbit anti-mite antibody, etc. [Immunochemistry, 8, 871 (1971)], (ii) assay of the antigeneic activity of each fraction by radioimmunoassay using rabbit anti-mite serum, (iii) assay of the allergen activity of each fraction on the basis of skin reaction activity, (iv) assay of the allergen activity of each fraction on the basis of mite allergy patient leukocyte histamine release activity, and other means. For example, the following methods can be used.

The mite antigen is subjected to gel filtration on Ultrogel AcA54 (produced by LKB Co.). The elution pattern is monitored on the basis of reactivities (ELISA) to mite asthmatic patient serum specific IgG and IgE and to rabbit anti-mite antibody, and patient leukocyte histamine release capability; fractionation is performed while using protein content and absorbance at 280 nm as guide parameters.

With respect to the fractions which show high response in ELISA using patient serum specific IgG and IgE and rabbit anti-mite antibody, and which possesses high capability of leukocyte histamine release and high skin reaction activity, the antigen component is separated using preparative disc SDS-PAGE. For extracting the desired antigen component from gel, for instance, shaking diffusion and electric elution are conducted using a 0.1% SDS solution, and the SDS used for extraction is removed by passing through the ion exchange resin AG11A8 (produced by Bio-Rad Laboratories). The mite allergen thus obtained is purified and isolated to the extent that is substantially free of any other mite proteins.

[Application as remedy for mite allergic diseases]

The purified and isolated mite allergen of the present invention is valuable as a remedy for hyposensitization therapy for mite allergic diseases.

Here, mite allergic diseases involve all allergic diseases that are caused by mite specific antigens, such as atopic bronchial asthma, allergic rhinitis, allergic conjunctivitis and atopic dermatitis.

The purified and isolated mite allergen obtained by the above-mentioned method is concentrated and then collected in the form of a solution or syrup, or concentrated, dried and then collected in the form of powder; it is then used as a remedy for hyposensitization therapy for mite allergic diseases. The remedy for hyposensitization therapy for mite allergic diseases can be used as it is, or can be used in formulation with ordinary adjuvants and various additives such as stabilizers, excipients, dissolution aids, emulsifiers, buffers, analgesics, preservatives and colorants as necessary.

The remedy for hyposensitization therapy for mite allergic diseases can be administered via ordinary routes of administration, for example, per os, intracutaneous, subcutaneous, intramuscular and intraperitoneal injection.

The remedy for hyposensitization therapy for mite allergic diseases can also be used in the form of a percutaneous or permucosal agent such as a troche, a sublingual tablet, an ophthalmic solution, an intranasal spray, a poultice, a cream or a lotion. It is administered at an appropriate dose and administration frequency chosen according to the route of administration, symptoms and other aspects so that the dose per adult in each administration is less than about 20 $\mu$g once a week.

Also, the remedy for hyposensitization therapy is valuable not only as a remedy but also as a preventive drug for mite allergic diseases. The remedy for hyposensitization therapy can be administered safely to humans since it does not induce anaphylactic reaction.

[Application as diagnostic drug for mite allergic diseases]

The purified and isolated mite allergen of the present invention is valuable as a diagnostic drug for mite allergic diseases.

Accordingly, the purified and isolated mite allergen is used as a titration reagent to titrate each of a given amount of patient blood and a given amount of a blood cell suspension prepared by suspending in a buffer a blood cell fraction obtained by centrifugation of patient blood, and this is followed by assay of the amount of histamine released from basophils (a type of leukocytes) in response to allergen stimulation [Journal of Japanese Society of Allergology: 33, 692 (1984)/Journal of Japanese Society of Allergology: 33, 733 (1984)].

In this histamine release titration, assay is made of the amount of histamine released at a point corresponding to 50% of the maximum release amount (inflexion point of the titration curve). In this titration:

(i) the allergen sensitivity of the patient is determined directly from the titration value of the blood cell suspension, and (ii) the titration value of blood is normally higher than that of the blood cell suspension because an IgG antibody (blocking antibody) capable of allergen neutralization is present in blood plasma.

Therefore, blocking antibody titer can be obtained from the size of the shift of the blood titration curve from the blood cell suspension titration curve. As shown in Table 1, it is possible to make accurate diagnoses of mite allergy on the basis of sensitivity and this blocking antibody titer. The purified and isolated mite allergen is also valuable in monitoring the hyposensitization therapeutic effect.

TABLE 1

| | | sensitivity | blocking antibody |
|---|---|---|---|
| 1. | patients with mite allergy | positive | negative |
| 2. | patients with mite allergy suceeding in hyposensitization therapy | positive | positive |
| 3. | healthy man possessing IgE antibody (naturally hyposensitized) | positive | positive |
| 4. | healthy man | negative | negative |

[Allergen activity tests and anaphylaxis induction tests]

The following experiments revealed that the purified and isolated mite allergen of the present invention possesses allergen activity and is free of any anaphylaxis induction property.

Experiment 1

100 $\mu$g of Dfb-94, Dfb-40, Dfb-16 or Dfb-14 in conjunction with Freund's complete adjuvant (produced by Difco Laboratories) was intraperitoneally injected into two BALB/c mice (4 weeks of age) for the first immunization at 0 week. Booster immunization was conducted at 2 and 4 weeks following the first immunization.

The anti-Dfb-94, anti-Dfb-40, anti-Dfb-16 and anti-Dfb-14 antibody titer in mouse sera showed a clear increase; sufficient immunogenicity was found. Based on these findings, it was judged that these allergens are capable of blocking antibody induction and can thus be used as a therapeutic antigen. As an example, FIG. 1 shows the results of an immunogenecity test of Dfb-94.

Experiment 2

Figure 2:
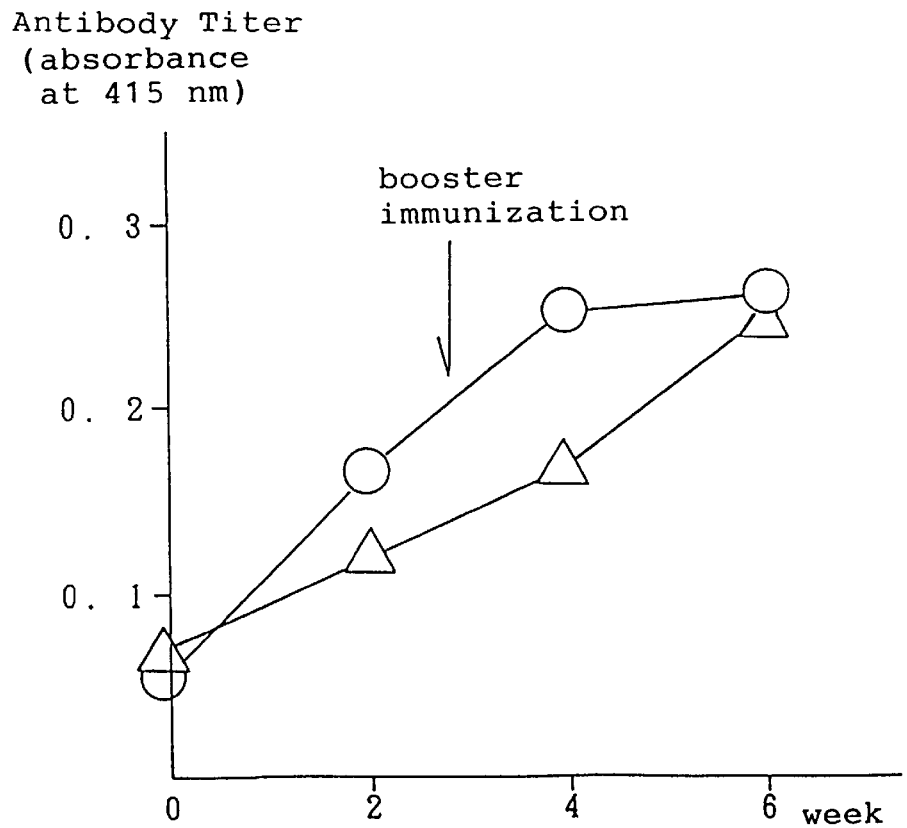
FIG. 2 shows changes in antibody titer in guinea pigs immunized with Dfb-94. The circles and triangles represent samples.

1 mg of Dfb-94, Dfb-40, Dfb-16 or Dfb-14 in conjunction with alum was intraperitoneally injected into two guinea pigs for the first immunization at 0 week. Booster immunization was conducted at 3 weeks following the first immunization. As a control, physiological saline in conjuction with alum was intraperitoneally injected into one guinea pig in the same manner as above. The anti-Dfb-94, anti-Dfb-40, anti-Dfb-16 and anti-Dfb-14 antibody titer in guinea pig sera showed a clear increase; sufficient immunogenicity was found. However, no anaphylactic symptoms were noted in the observation immediately after booster immunization at 3 weeks. Based on these finding, Dfb-94, Dfb-40, Dfb-16 and Dfb-14 were judged to be free of any anaphylaxis induction property. As an example, FIG. 2 shows the results in immunogenicity test of Dfb-94.

EXAMPLES

The present invention is hereinafter described in more detail by means of the following examples, but the present invention is not by any means limited by these examples.

Example 1
(Preparation of crude mite antigen)

Under conditions of 26±2° C. temperature and 75% RH humidity, *Dermatophagoides farinae* was grown in animal food M for rats, mice and hamsters (produced by Oriental Yeast) to a mite density of about 20,000 to 30,000 mites/gram of medium. After the mites in the mite culture were killed by freezing, a 10-fold amount by weight of saturated sodium chloride solution was added to 12.2 kg of the mite culture, followed by gentle thorough stirring. After being allowed to stand at 4° C. for 1 hour, the mixture was centrifuged at 4° C. and 3000 rpm for 30 minutes to suspend the mites on the surface of the supernatant, which were then recovered by suction. To 1.7 kg of the mites thus obtained, a half amount by weight of PBS was added, and the mixture was thoroughly ground using a mortar. To this ground product, additional PBS was added to reach a 2-fold final amount, followed by 1 hour of extraction with occasional stirring. This suspension was centrifuged at 4° C. and 8000 rpm for 30 minutes. After the supernatant was dialyzed against deionized water, the insoluble substances were removed by centrifugation at 4° C. and 8000 rpm for 30 minutes, and the supernatant was lyophilized to yield 19.6 g of a crude mite antigen (Dfb).

Example 2
(Fractionation of crude mite antigen using Ultrogel AcA54 (Produced by LKB Co.))

Figure 3:
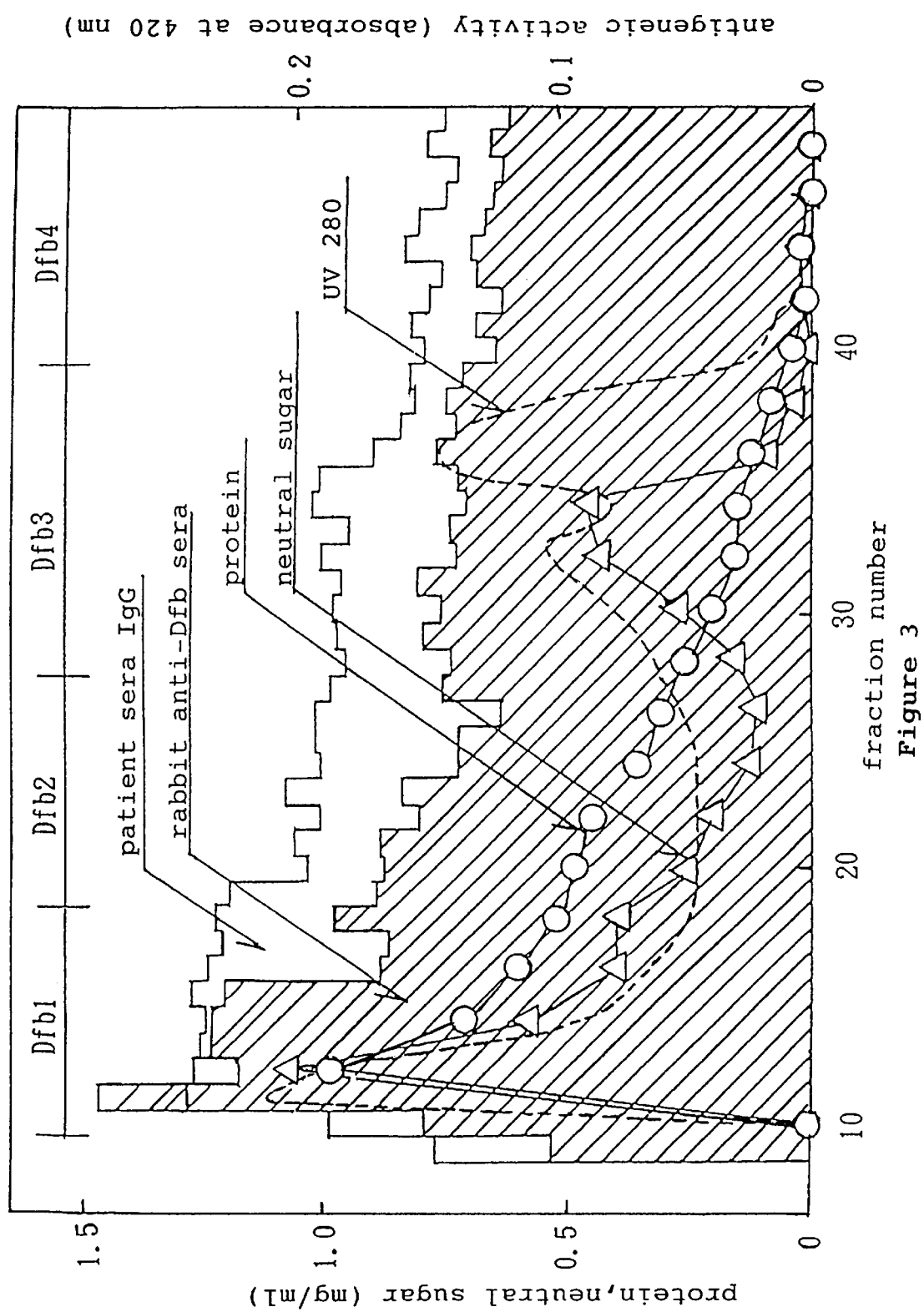
FIG. 3 shows results of gel filtration of a crude mite antigen on Ultrogel AcA54. The circles represent protein concentration in the samples; the triangles represent neutral sugar concentration in the samples.

30 ml of 2% (w/v) crude mite antigen was centrifuged at 2000 rpm for 10 minutes, and the insoluble substances were removed. This product was applied to a column of Ultrogel AcA54 (produced by LKB Co., column size 4.4×75.0 cm), previously equilibrated with a 0.9% NaCl solution, followed by fractionation with a fraction volume of 32 ml at a flow rate of 2 ml/minute while monitoring the progress of fractionation by UV absorbance at 280 nm. The antigen activity of each fraction was determined by ELISA of patient serum and rabbit anti-crude mite antigen serum. The distributions of protein and neutral sugar were determined by the Folin-Lowry method and the phenol sulfuric acid method, respectively. On the basis of the allergen distribution determined by a previous assay on an analytical scale and the UV 280 nm absorption pattern, the crude mite antigen was fractionated into four fractions (Dfb 1 through 4) (FIG. 3). The yields of these fractions from 1 g of Dfb were 506 mg of Dfb1, 148 mg of Dfb2, 33 mg of Dfb3 and 3 mg of Dfb4.

The four fractions thus obtained using Ultrogel AcA54 (produced by LKB Co.) were subjected to a skin reaction test in asthmatic patients. As a result, of the four fractions (Dfb1 through 4), the Dfb2 fraction showed the highest skin reaction activity, and this fraction also showed the highest allergen activity in the histamine release test (Table 2). The data in Table 2 show the average diameter of the skin reaction activity (erythema), each representing the ranges shown below:

−: 0 to less than 10 mm;
±: 10 to less than 20 mm;
+: 20 to less than 30 mm;
++: 30 to less than 40 mm; and
+++: not less than 40 mm.

Judging from this finding, this Dfb2 fraction is considered to contain large amounts of main allergens of the crude mite antigen.

TABLE 2

| Patient | H.O. | Mite | Crude mite antigen | Dfb1 | Dfb2 | Dfb3 | Dfb4 |
|---------|------|------|--------------------|------|------|------|------|
| 1 | +++ | +++ | +++ | +++ | +++ | | |
| 2 | +++ | ± | + | + | ++ | | |
| 3 | ++ | + | + | + | ++ | | |
| 4 | ± | ± | ± | ± | + | | |
| 5 | ++ | ++ | +++ | | | ++ | ± |
| 6 | − | ++ | | | | − | − |
| 7 | | | | ± | ± | − | |

Example 3
(Detection of allergen components of the Dfb2 fraction by SDS-PAGE, Western blot and immunostaining)

The Dfb2 fraction, showing the highest allergen activity, was subjected to SDS-PAGE. The SDS-PAGE was not affected, whether the sample was reduced or not, except that a band corresponding to a molecular weight of about 100 k disappeared when the sample was reduced. The molecular weight distribution of the Dfb2 fraction as determined by SDS-PAGE broad from 14 k to 94 k.

This fraction was then subjected to Western blot and immunostaining with Auro Dye (produced by Janssen Pharmaceutica). Reaction took place with various components in the Dfb2 fraction, differing among the patients, but the 94 k, 60 k, 40 k, 16 k and 14 k components reacted with very high frequencies. Judging from this finding, it is concluded that these components are the main allergen components of Dfb2, the fraction showing the highest allergen activity.

Figure 4:
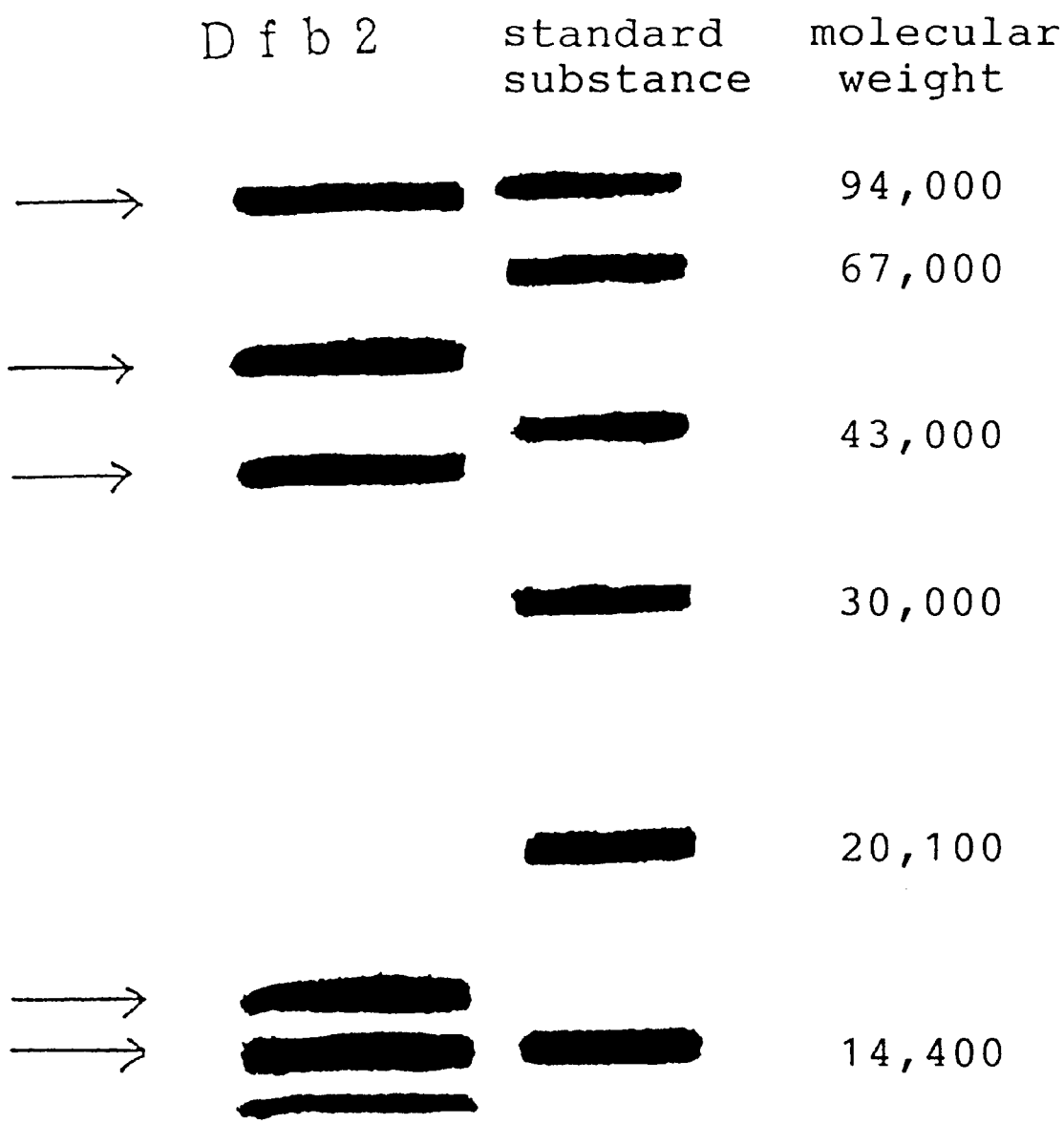
FIG. 4 shows an electrophoretogram of Dfb-2 and a standard substance on a large sized disc SDS-polyacrylamide gel.

Example 4
(Separation, extraction and purification of allergen by large sized disc SDS-PAGE) The 94 k, 60 k, 40 k, 16 k and 14 k components, suspected to be allergens in the Dfb2 fraction, were purified by large sized disc SDS-PAGE. 20 mg of Dfb2 and a standard substance were subjected to large sized disc SDS-PAGE. The electrophoretogram is shown in FIG. 4. The gel portions considered to correspond to the 94 k, 60 k, 40 k, 16 k and 14 k allergens, indicated by arrow in FIG. 4, were each cut out and subjected to shaking diffusion or electric elution to extract the allergens from the gel.

In cases where purification was insufficient, purification was repeated as necessary using 10% T gel or 12.5% T gel.

The yields of the separated and purified components from Dfb2 (148 mg) were 1.2 mg of Dfb-94, 1.8 mg of Dfb-60, 2.1 mg of Dfb-40, 6.5 mg of Dfb-16 and 7.7 mg of Dfb-14.

Example 5
(Confirmation of allergenicity of the components)

Figure 5:
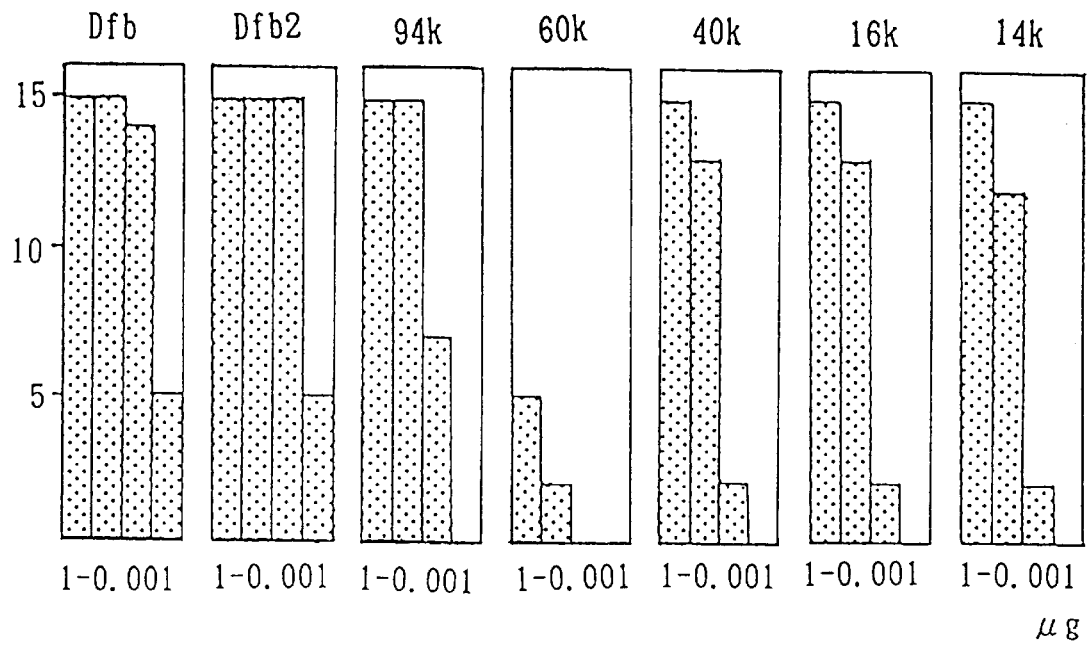
FIG. 5 shows results of a spot immunostaining test using Dfb-94, Dfb-60, Dfb-40, Dfb-16, and Dfb-14. The number of patients in each test is plotted on the y axis.
Figure 5:
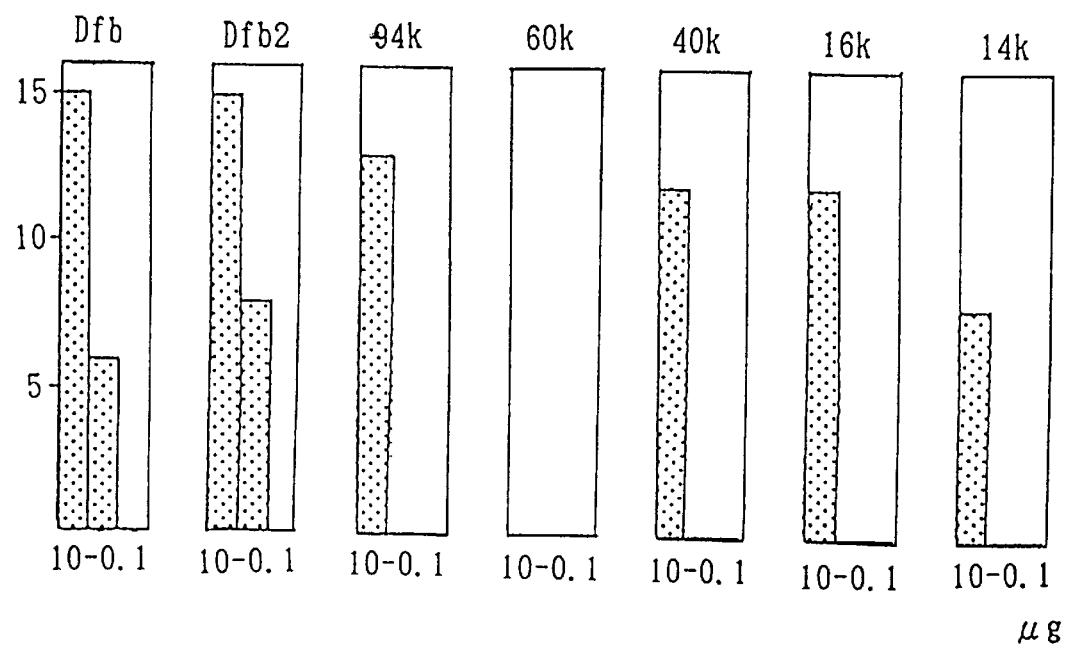

The components Dfb-94, Dfb-60, Dfb-40, Dfb-16 and Dfb-14 obtained by purification and isolation above were subjected to a spot immunostaining test on a nitrocellulose sheet using sera of 15 asthmatic patients. The results are shown in FIG. 5. These components reacted to the serum IgG of the 15 asthmatic patients at very high frequencies. However, Dfb-60 was low in reaction frequency, though it reacted to the patient serum IgG. Similarly, Dfb-94, Dfb-40, Dfb-16 and Dfb-14 all reacted with the patient serum IgE at high frequencies of not less than 8 patients. It was thus confirmed that these Dfb-94, Dfb-40, Dfb-16 and Dfb-14 components were main allergens derived from the mite antigen. Since Dfb-60 did not react with the asthmatic patient serum IgE at all, the possibility of its identity as an allergen was judged low. To summarize, previously unreported new and main allergens were detected, separated, and purified from the crude mite antigen by gel chromatography and large sized disc SDS-PAGE.

Example 6

(Immunoassay by cross immunoelectrophoresis (CIE))

To determine the immunological purity of the purified and isolated mite allergen obtained in Example 4, two-dimensional immunoelectrophoresis was conducted. As a result, Dfb-94 formed a single sharp precipitation band with rabbit anti-mite serum. This finding confirms that the Dfb-94 allergen is very uniform at the antigen level. Dfb-40 also formed a single sharp precipitation band, and it was found uniform at the antigen level with respect to rabbit antiserum. Dfb-16 was found to have been purified fairly uniformly. Dfb-14 also formed only a single precipitation band. The CIE results confirm that very uniform purification was achieved by large sized disc SDS-PAGE.

Example 7

(Composition analysis)

Dfb-94, Dfb-40, Dfb-16 and Dfb-14 were analyzed for composition. Their amino acid compositions were determined by the method described below.

200 µl of a 0.2% sample solution was mixed with 200 µl of 12N HCl and hydrolyzed at 110° C. in a sealed $N_2$-saturated test tube for 24 hours. After evaporating the hydrolysate to dryness, a small amount of water was added, and this was followed by re-evaporation to dryness. This procedure was repeated in three cycles to remove the hydrochloric acid. The resulting dry product was dissolved in 1 ml of a dilution buffer for an amino acid analyzer. This solution was then assayed using an amino acid analyzer (produced by Beckman Co.).

Total neutral sugar was quantitatively determined by the phenol sulfuric acid method using glucose as reference substance.

Each neutral sugar and amino sugar were quantitatively determined by the GLC method after the sample was hydrolyzed at 100° C. in 4N TFA (trifluoroacetic acid) for 4 hours, reduced with $NaBH_4$, and then acetylated by heating at 100° C. for 4 hours in the presence of acetic anhydride.

As a result, Dfb-94, Dfb-40, Dfb-16 and Dfb-14 were found to have the following compositions shown in Tables 3 through 6.

TABLE 3

Composition of Dfb-94

1. Amino acid (total 3260.1 nmol/mg)

| | | | | | | | |
|---|---|---|---|---|---|---|---|
| Asp | 413.2; | Thr | 461.0; | Ser | 298.0; | | |
| Glu | 521.4; | Gly | 127.8; | Ala | 150.4; | | |
| Cys | 21.5; | Val | 212.5; | Met | 19.4; | | |
| Ile | 77.0; | Leu | 370.4; | Tyr | 3.3; | | |

TABLE 3-continued

Composition of Dfb-94

| | | | | | |
|---|---|---|---|---|---|
| Phe | 55.7; | His | 30.3; | Lys | 322.2; |
| Arg | 68.3; | Pro | 107.7 | | |

2. Neutral sugar (total 3154.9 nmol/mg)

| | | | | | |
|---|---|---|---|---|---|
| Fuc | 216.5; | Ara | 426.7; | Xyl | 490.0; |
| Gal | 350.0; | Man | 1671.7; | Glc | — |

3. Amino sugar (total 265.2 nmol/mg)

| | |
|---|---|
| HexNAc | 265.2 |

TABLE 4

Composition of Dfb-40

1. Amino acid (total 6792.9 nmol/mg)

| | | | | | |
|---|---|---|---|---|---|
| Asp | 613.1; | Thr | 361.0; | Ser | 483.3; |
| Glu | 846.4; | Gly | 676.4; | Ala | 875.4; |
| Cys | 81.7; | Val | 511.1; | Met | 10.7; |
| Ile | 273.6; | Leu | 540.4; | Tyr | 93.3; |
| Phe | 212.5; | His | 147.6; | Lys | 433.7; |
| Arg | 334.7; | Pro | 298.0 | | |

2. Neutral sugar (total 797.4 nmol/mg)

| | | | | | |
|---|---|---|---|---|---|
| Fuc | 12.2; | Ara | 28.7; | Xyl | 153.3; |
| Gal | 79.4; | Man | 469.4; | Glc | 54.4 |

3. Amino sugar (total 67.4 nmol/mg)

| | |
|---|---|
| HexNAc | 67.4 |

TABLE 5

Composition of Dfb-16

1. Amino acid (total 6378.4 nmol/mg)

| | | | | | |
|---|---|---|---|---|---|
| Asp | 753.6; | Thr | 569.3; | Ser | 530.0; |
| Glu | 728.1; | Gly | 523.3; | Ala | 456.8; |
| Cys | 64.4; | Val | 428.3; | Met | 12.7; |
| Ile | 310.2; | Leu | 424.5; | Tyr | 164.5; |
| Phe | 191.7; | His | 122.4; | Lys | 407.0; |
| Arg | 350.2; | Pro | 341.4 | | |

2. Neutral sugar (total 778.4 nmol/mg)

| | | | | | |
|---|---|---|---|---|---|
| Fuc | 47.6; | Ara | 48.0; | Xyl | 320.7; |
| Gal | 182.7; | Man | — | Glc | 179.4 |

3. Amino sugar (total 290.5 nmol/mg)

| | |
|---|---|
| HexNAc | 290.5 |

TABLE 6

Composition of Dfb-14

1. Amino acid (total 6601.5 nmol/mg)

| | | | | | |
|---|---|---|---|---|---|
| Asp | 722.8; | Thr | 715.4; | Ser | 577.5; |
| Glu | 870.2; | Gly | 471.4; | Ala | 576.9; |
| Cys | 59.4; | Val | 355.8; | Met | 76.4; |
| Ile | 281.3; | Leu | 554.1; | Tyr | 15.5; |

TABLE 6-continued

Composition of Dfb-14

| Phe | 72.8;  | His | 130.2; | Lys | 500.7; |
|-----|--------|-----|--------|-----|--------|
| Arg | 237.1; | Pro | 384.0  |     |        |

2. Neutral sugar (total 564.3 nmol/mg)

| Fuc | 37.8; | Ara | 20.0; | Xyl | 219.3; |
|-----|-------|-----|-------|-----|--------|
| Gal | 66.1; | Man | 32.8; | Glc | 188.3  |

3. Amino sugar (total 184.2 nmol/mg)

| HexNAc | 184.2 |
|--------|-------|

From these data, it is evident that Dfb-94, Dfb-40, Dfb-16 and Dfb-14 contained sugar at about 60%, about 15%, about 20% and about 13%, respectively. Although Dfb-16 and Dfb-14 have a molecular weight similar to that of Der f II, a previously reported main allergen derived from mites, Der f II is different from Dfb-16 and Dfb-14 in that the former is a protein allergen while the latter two are sugar protein allergens.

Example 8
(Preparation of antigen preparation for hyposensitization therapy)

Dfb-94, Dfb-40, Dfb-16 or Dfb-14 is dissolved in a 0.9% sodium chloride solution supplemented with 0.5% phenol to make a concentration of 1 mg/ml; the resulting solution is used as the original solution to prepare an antigen preparation for hyposensitization therapy.

Example 9
(Preparation of titration reagent for mite allergy diagnosis)

Dfb-94, Dfb-40, Dfb-16 or Dfb-14 is dissolved in Hanks' solution to make a concentration of 1 mg/ml; the resulting solution is used as the original solution to prepare a titration reagent for mite allergy diagnosis.

What is claimed is:

1. A purified and isolated mite allergen substantially free of any other mite proteins characterized by the following physicochemical and biological properties:
   ① being contained in extracts of mite;
   ② glycoprotein containing about 15% sugar;
   ③ a molecular weight of about 40,000 as determined by SDS-polyacrylamide gel electrophoresis; and
   ④ possessing allergen activity.

2. The purified and isolated mite allergen according to claim 1, wherein said mite is *Dermatophagoides farinae*.

3. The purified and isolated mite allergen according to claim 1, wherein the protein has the following amino acid, neutral sugar and amino sugar composition:

nanomoles amino acids, of 6792.9 nanomoles proteins:
  Asp 613.1;
  GLU 846.4;
  Cys 81.7;
  Ile 273.6;
  Phe 212.5;
  Arg 334.7;
  Thr 361.0;
  Gly 676.4;
  Val 511.1;
  Leu 540.4;
  His 147.6;
  Pro 298.0;
  Ser 483.3;
  Ala 875.4;
  Met 10.7;
  Tyr 93.3;
  Lys 433.7;

nanomoles neutral sugar, of 797.4 nanomoles:
  Fuc 12.2;
  Gal 79.4;
  Ara 28.7;
  Man 469.4;
  Xyl 153.3;
  Glc 54.4;

nanomoles amino sugars, of 67.4 nanomoles:
  HexNAc 67.4.

4. A pharmaceutical composition for the treatment of mite allergic diseases which comprises as the active ingredient a pharmaceutically effective amount of the purified and isolated mite allergen according to claim 1, and at least one pharmaceutically acceptable carrier or diluent.

5. A diagnostic composition for mite allergic diseases which comprises as the active ingredient a diagnostically effective amount of the purified and isolated mite allergen according to claim 1.

6. A method of treatment for mite allergic diseases which comprises an administration of a pharmaceutically effective amount of the purified and isolated mite allergen according to claim 1.

7. The method of treatment for mite allergic diseases according to claim 6, which is a hyposensitization therapy.

* * * * *